(12) United States Patent
Pinter et al.

(10) Patent No.: US 8,428,699 B2
(45) Date of Patent: Apr. 23, 2013

(54) APPARATUS, METHOD AND COMPUTER PROGRAM FOR MEASURING PROPERTIES OF AN OBJECT

(75) Inventors: Robert Pinter, Aachen (DE); Jeroen Adrianus Johannes Thijs, Waldfeucht (DE); Jens Muehlsteff, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 251 days.

(21) Appl. No.: 12/808,395

(22) PCT Filed: Dec. 16, 2008

(86) PCT No.: PCT/IB2008/055339
§ 371 (c)(1),
(2), (4) Date: Jun. 16, 2010

(87) PCT Pub. No.: WO2009/081331
PCT Pub. Date: Jul. 2, 2009

(65) Prior Publication Data
US 2010/0305460 A1     Dec. 2, 2010

(30) Foreign Application Priority Data
Dec. 19, 2007   (EP) .................................... 07123703

(51) Int. Cl.
*A61B 5/04*     (2006.01)
(52) U.S. Cl.
USPC ........................................................ 600/509
(58) Field of Classification Search ........................ None
See application file for complete search history.

(56) References Cited

U.S. PATENT DOCUMENTS

| | | | |
|---|---|---|---|
| 4,320,766 | A | 3/1982 | Alihanka et al. |
| 4,895,169 | A | 1/1990 | Heath |
| 5,467,768 | A | 11/1995 | Suda et al. |
| 5,824,033 | A | 10/1998 | Ferrari |
| 6,228,033 | B1 | 5/2001 | Koobi et al. |
| 6,470,893 | B1 | 10/2002 | Boesen |
| 6,577,893 | B1 | 6/2003 | Besson et al. |
| 2004/0106967 | A1* | 6/2004 | Von Arx et al. .................. 607/60 |
| 2004/0123667 | A1 | 7/2004 | McGrath |
| 2005/0043608 | A1 | 2/2005 | Haj-Yousef |
| 2007/0276294 | A1* | 11/2007 | Gupta et al. ................... 600/594 |

FOREIGN PATENT DOCUMENTS

| WO | 03045236 | A2 | | 6/2003 |
|---|---|---|---|---|
| WO | 2007010422 | A2 | | 1/2007 |
| WO | WO 2007010460 | A2 | * | 1/2007 |
| WO | 2007023426 | A2 | | 3/2007 |
| WO | 2008-036404 | A2 | | 3/2008 |

OTHER PUBLICATIONS

"The Use of a Two Channel Doppler Radar Sensor for the Characterization of Heart Motion Phases" Proceedings of the IEEE EMBS Conf. New York City, USA Aug. 30-Sep. 3, 2006.

* cited by examiner

*Primary Examiner* — Carl H Layno
*Assistant Examiner* — Paula J Stice (57) ABSTRACT

An apparatus measures properties of an object such as a heart in a patient (2). The apparatus includes an antenna (3, 4) for sending and/or receiving electromagnetic waves to and/or from the object (2) for measuring a property of the object. The antenna (3, 4) includes an electrically conductive element for functioning as an electrode for measuring a further property of the object. The electromagnetic waves are reflected by the object, causing a Doppler shift. The apparatus uses this shift to provide mechanical information about the object and uses the electrode to provide electrical information about the object, such as an electrocardiogram.

18 Claims, 5 Drawing Sheets

APPARATUS, METHOD AND COMPUTER PROGRAM FOR MEASURING PROPERTIES OF AN OBJECT

FIELD OF THE INVENTION

The invention relates to an apparatus, a method and a computer program for measuring properties of an object

BACKGROUND OF THE INVENTION

U.S. Pat. No. 6,228,033 B1 discloses an apparatus and a method for measuring three important physiological systems, circulations, breathing, and body water compartments, of a patient. More specifically an apparatus and a method for a continuous simultaneous/synchronized and noninvasive measurement of heart pump function, elastic properties of the vascular system, systemic vascular resistance, breathing capacity, and body water compartments through the combined use of bioimpedance and continuous blood pressure measurement techniques and, optionally, spirometry and/or plethysmography are disclosed. This apparatus and method need a large number of sensors for measuring the different properties of a patient.

While on the one hand it seems to be a reasonable approach to use a multitude of measurements with a large number of sensors, this may easily become a totally overloaded system. A large number of sensors leads to an extremely complicated handling of the system. In particular, in Personal Healthcare applications the patients do not exhibit sufficient medical or technical training and often have impaired vision and reduced motor skills, so they are not able to use properly a system with such a complicated handling.

SUMMARY OF THE INVENTION

It is therefore an object of the present invention to provide an apparatus, a method and a computer program for measuring properties of an object, which reduce the number of sensors needed for determining different properties of the object.

In an aspect of the present invention an apparatus for measuring properties of an object is provided, wherein the apparatus comprises an antenna for sending and/or receiving electromagnetic waves to and/or from the object for measuring a property of the object, wherein the antenna comprises an electrically conductive element for functioning as an electrode for measuring a further property of the object.

The invention is based on the idea that, since the antenna, which sends and/or receives electromagnetic waves from the object for measuring a property of the object, comprises an electrically conductive element for functioning as an electrode for measuring a further property, the antenna can measure different properties of the object by functioning as antenna and, in addition, as electrode, wherein the number of sensors for determining properties of the object can be reduced.

Properties of the object can, for example, be regarded as characteristics or conditions of the object. A property of the object is, for example, an electrophysiological property like an electrocardiogram, which is preferably measured by using the electrically conductive element functioning as an electrode. A further property is, for example, the mechanical activity, in particular, the movement, of the object, which is preferentially a heart and which is preferentially measured by sending and receiving electromagnetic waves to and from the object.

The apparatus can comprise one or several of the antenna comprising the electrically conductive element for functioning as electrode. The use of several of the antennas allows measuring the further property, in particular an electrophysiological property, with several of the electrically conductive elements acting as electrode, for example, by performing an impedance cardiography or bio-impedance measurements. Furthermore, for example, one of the antennas can send electromagnetic waves, wherein another antenna can receive the electromagnetic waves reflected from the object.

The electrically conductive element is preferentially a metal plate. Since the electrically conductive element is preferentially a metal plate, the electrically conductive element can be used for a patch antenna or as part of a patch antenna, i.e. the antenna is preferentially a patch antenna, wherein a metal plate of the patch antenna is preferentially used as an electrode for measuring a property, in particular an electrophysiological property, of the object, in particular simultaneously.

It is preferred that the electrically conductive element is adapted for an electrocardiogram measurement.

It is further preferred that the object is a moving object, wherein the antenna is adapted for emitting electromagnetic waves, which are reflectable by the moving object, and wherein the antenna is adapted for receiving electromagnetic waves reflected from the moving object. This allows determining the movement of the object or of a part of the object in dependence on electromagnetic waves reflected from the moving object. The object is preferentially a human heart, wherein the electromagnetic waves are reflected from a wall, in particular from a part of the wall, of the human heart. Thus, the movement of the wall of a human heart can be determined, preferentially simultaneously with measuring an electrocardiogram. It is therefore possible to determine the electrical stimulation of the myocardium (electrocardiogram) and the conversion of this stimulation into mechanical activity by measuring the movement of the human heart. Thus, the electrical stimulation of a heart and the mechanical reaction to the electrical stimulation can be determined by this preferred embodiment of the apparatus, in particular with a single sensor. In particular, it can be determined how fast the heart muscle responds mechanically to the electrical excitation, which is important for non-invasive cuff-less blood pressure measurements and for determining arterial stiffness.

In a preferred embodiment, the apparatus comprises a plurality of the antennas, wherein at least one of the plurality of the antennas is adapted for sending and/or receiving electromagnetic waves at a frequency, which differs from a frequency of electromagnetic waves of another of the plurality of antennas. This allows operating the antennas simultaneously.

Preferentially, the apparatus comprises a movement determination unit for determining movement information indicative of a movement of the object in dependence on received electromagnetic waves reflected from the moving object using the Doppler effect. This allows determining movement information indicative of the movement of the object, in particular, the movement of the object itself, accurately and with low computational efforts.

The apparatus preferentially comprises several of the antennas which are adapted for forming a beam of the electromagnetic waves, in particular by using a phased array of the antennas. This allows directing the electromagnetic waves into regions, to which or from which electromagnetic waves are to be transferred or are to be received. Furthermore, the antenna can be sensitive in specific directions while suppressing incoming signals from other directions. Thus, if, for example, adjustable phase shifters are used, it is possible to scan a given area for incoming signals without having to move the antennas mechanically.

It is further preferred that the object is an inner object located within an outer object, wherein the antenna is attachable to a surface of the outer object for preventing a relative movement between the surface, in particular the skin of a patient, and the antenna. In particular, the electrically conductive element is attached to the surface, in particular the skin, of a patient being the outer object. For example, the antenna, in particular the electrically conductive element, can be stickable to the surface of the outer object, in order to adhesively attach the antenna to the surface of the outer object. This ensures that there is no relative motion between the surface and the antenna. Especially, if the Doppler effect is used for determining a mechanical motion of the inner object, in particular, of the heart wall, a relative movement between the surface of the outer object and the antenna could distort the electromagnetic waves received by the antenna, because the electromagnetic waves are generally reflected also at the surface, which may cause additional Doppler shifts.

The electrically conductive element and/or the antenna are preferentially adapted such that the further property, in particular the electrophysiological property, of the object is measurable by detecting an electrical signal by the electrically conductive element having a frequency, which differs from the frequency of the electromagnetic waves sent and/or received by the antenna. In particular, the frequency of the electromagnetic waves is several orders of magnitude higher than the frequency of the electrical signal for measuring the further property, in particular the electrophysiological property. Thus, electrical signals of the further measurement, in particular of the electrophysiological measurement, wherein the electrically conductive element acts as an electrode, and electrical signals of the electromagnetic waves of the antenna can easily be separated, for example, by using filters, and the further measurement, in particular the electrophysiological measurement, and a measurement using the electromagnetic waves, in particular a measurement of mechanical properties like the movement of a wall, in particular of a part of the wall, of the object, can be performed simultaneously.

It is preferred that the object is a heart of a patient, in particular, a human patient or an animal patient, wherein the apparatus comprises a property determination unit for determining the blood pressure and/or the arterial stiffness based on an electrocardiac signal measured by the electrically conductive element functioning as an electrode of at least two of the antennas and based on a mechanical activity of the heart determined from the electromagnetic waves sent to and received from the object by the at least two of the antennas. This allows determining the blood pressure and/or the arterial stiffness non-invasive and preferentially without a cuff.

In a further aspect of the present invention, a method for measuring properties of an object is provided, wherein an apparatus for measuring properties of an object is used, the apparatus comprising an antenna comprising an electrically conductive element, wherein electromagnetic waves are sent and/or received to and/or from the object by the antenna for measuring a property of the object and wherein a further property of the object is measured by using the electrically conductive element as an electrode.

In a further aspect of the present invention, a computer program for measuring properties of an object is provided, wherein the computer program comprises program code means for causing a computer to carry out the steps of the method as defined in claim 11, when the computer program is run on a computer controlling an apparatus as defined in claim 1.

It shall be understood that the apparatus of claim 1, the method of claim 11 and the computer program of claim 12 have similar and/or identical preferred embodiments, in particular as defined in the dependent claims.

It shall be understood that preferred embodiments of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings

DETAILED DESCRIPTION OF EMBODIMENTS

Figure 1:
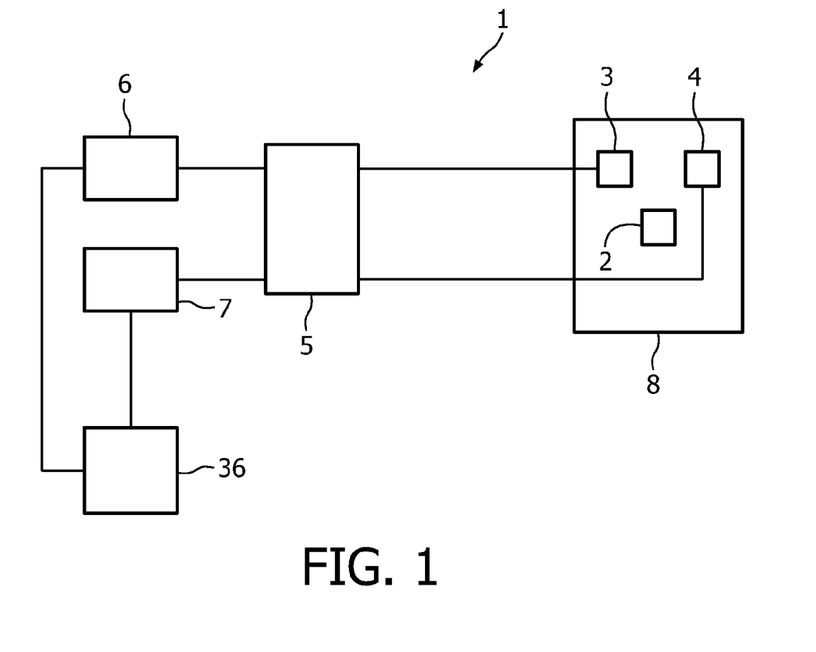
FIG. 1 shows schematically and exemplarily an apparatus for measuring properties of an object.

FIG. 1 shows schematically and exemplarily an apparatus 1 for measuring properties of an object. The apparatus 1 comprises, in this embodiment, two antennas 3, 4, which are attached to an outer object 8, in which an inner object 2 is located. In FIG. 1, the inner object 2 and the outer object 8 are shown schematically only. The outer object 8 is preferentially a patient with a heart 2. The antennas 3, 4 are preferentially attached to a surface of the outer object 8, in particular, to the skin of a human patient, such that the antennas 3, 4 do not move relative to the surface of the outer object 8, but the inner object 2, in particular the heart of a patient, may still move with respect to the position of the antennas 3, 4.

The antennas 3, 4 are, in this embodiment, patch antennas. The patch antenna 3 is schematically and exemplarily shown in FIG. 2. In this embodiment, the patch antenna 3 and the patch antenna 4 have the same construction. In another embodiment, different antennas can have different constructions. For example, different antennas can be adapted for providing different operation frequencies such that electromagnetic waves of different antennas can be separated, for example, by using filter units.

Figure 2:
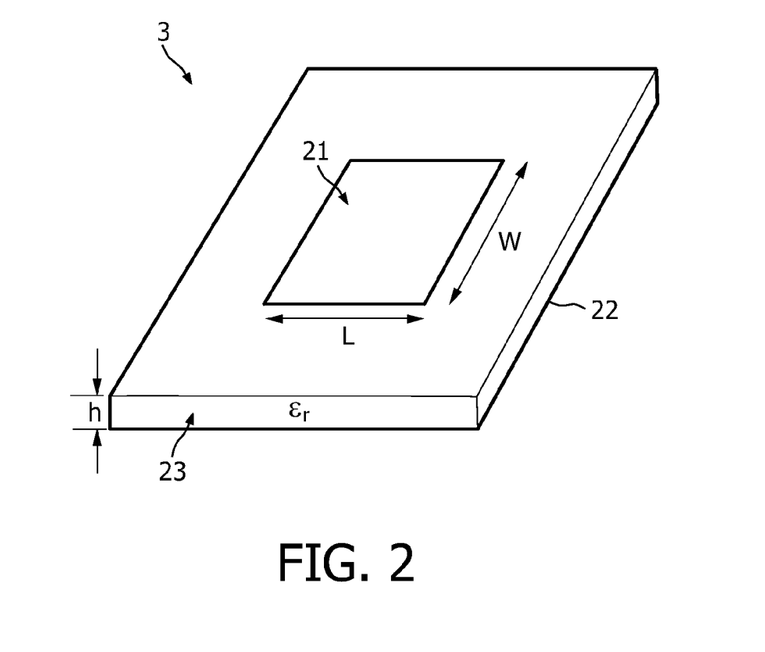
FIG. 2 shows schematically and exemplarily an antenna comprising an electrically conductive element.

Referring to FIG. 2, the patch antenna 3 comprises an electrically conductive element 21, which is, in this embodiment, a metal plate. The electrically conductive element 21 is attached to a non-conductive dielectric substrate 23 having a dielectric constant $\in_r$. The electrically conductive element 21 is preferentially stuck to the substrate 23. On the side of the substrate 23, which is opposite to the side, on which the electrically conductive element 21 is located, a ground plane 22 is arranged. Preferentially, also the ground plane 22 is stuck to the substrate 23.

Preferentially, the electrically conductive element 21 is in contact with the outer object 8, in particular, with the skin of a patient, during a measurement of properties of the inner object 2, wherein the electrically conductive element 21 acts as an electrode for electrophysiological measurements. Furthermore, the patch antennas 3, 4 are adapted for sensing and/or receiving electromagnetic waves to and/or from the inner object 2.

In a preferred embodiment, the patch antennas 3, 4 are adapted such that they have an operating frequency, which is suitable for investigations of the mechanical heart activity. Such an operating frequency is preferentially a frequency within the range of 2 to 3 GHz, further preferred within a range of 2.4 to 2.6 GHz, and is preferentially 2.45 GHz.

For adapting the patch antennas 3, 4, preferentially, the following equation is used:

$$W = \frac{1}{2 \cdot f_r \cdot \sqrt{\mu_0 \cdot \varepsilon_0}} \cdot \sqrt{\frac{2}{\varepsilon_r + 1}} = \frac{v_0}{2 \cdot f_r} \cdot \sqrt{\frac{2}{\varepsilon_r + 1}}. \quad (1)$$

In equation (1), W denotes the width of the electrically conductive element 21, $f_r$ denotes the operating frequency of the patch antenna 3, 4 and $v_0$ denotes the velocity of light in vacuum. Once the width W is calculated, an appropriate length of the electrically conductive element 21 can be determined with the help of the below mentioned equations. Actually, the length of the electrically conductive element 21 is virtually longer than the physical dimension, an effect that occurs due to the bending of the field lines at the edges of the patch. In order to take that into a count, the effective dielectric constant or the permittivity of the patch antenna 3, 4 is preferentially determined according to the following equation:

$$\varepsilon_{reff} = \frac{\varepsilon_r + 1}{2} + \frac{\varepsilon_r - 1}{2} \cdot \left(1 + \frac{12 \cdot h}{W}\right)^{-\frac{1}{2}} \quad (2)$$

wherein h is the height of the substrate 23.

The virtual lengthening $\Delta L$ of the electrically conductive element 21 can be determined by using following equation:

$$\frac{\Delta L}{h} = K \cdot \frac{(\varepsilon_{reff} + c_1) \cdot \left(\frac{W}{h} + c_2\right)}{(\varepsilon_{reff} - c_3) \cdot \left(\frac{W}{h} + c_4\right)} \quad (3)$$

wherein $c_1 \ldots c_4$ and K are constants. These constants have preferentially following values: $c_1$=0.3, $c_2$=0.264, $c_3$=0.258, $c_4$=0.8 and K=0.412. The constants are preferentially determined empirically in experiments. For more details with respect to equation (3) reference is made to Constantine A. Balanis: "Antenna theory—Analysis and Design", Second Edition 1997, John Wiley & Sons, Inc., which is herewith incorporated by reference.

Finally, the physical length L of the electrically conductive element 21 can be determined by following equation:

$$L = \frac{1}{2 \cdot f_r \cdot \sqrt{\varepsilon_{reff}} \cdot \sqrt{\mu_0 \cdot \varepsilon_0}} - 2\Delta L \quad (4)$$

For example, if the operating frequency is 2.45 GHz, if the height of the substrate 23 is 3 mm and if the dielectric constant or the permittivity of the substrate 23 is 4.2, a length of 29 mm and a width of 38 mm can be calculated for the electrically conductive element 21. This is about the size of a standard electrocardiography electrode.

The size of the electrically conductive element 21 could easily be reduced by using a substrate 23 with a higher permittivity or dielectric constant $\varepsilon_r$.

Figure 6:
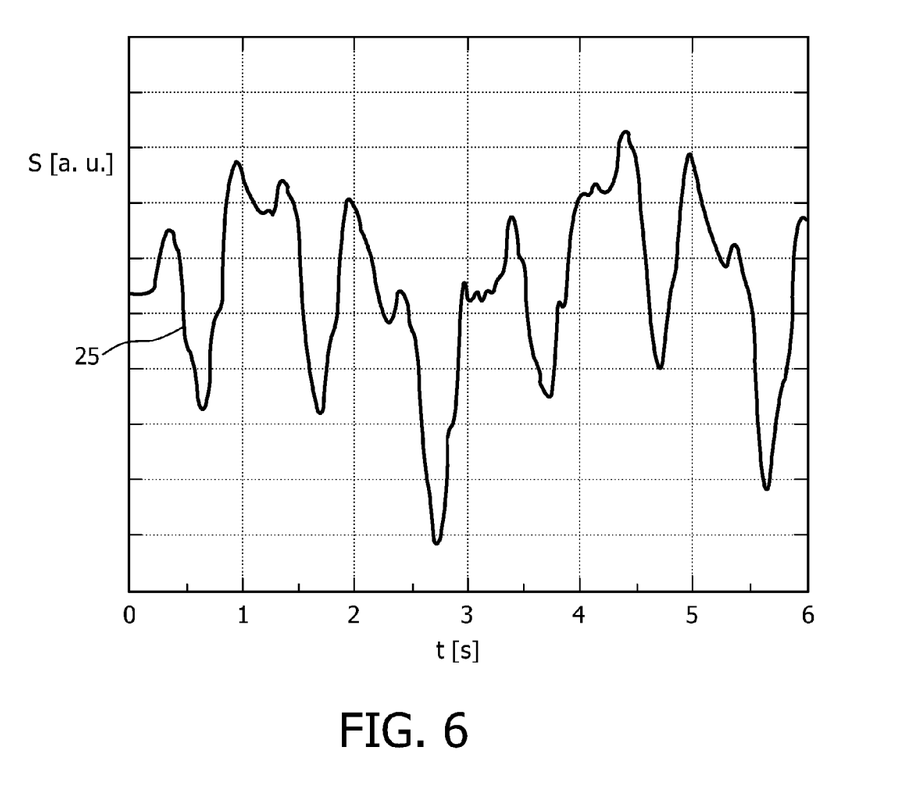
FIG. 6 shows schematically and exemplarily a Doppler radar signal and, FIG. 7 shows a flow chart exemplarily illustrating a method for measuring properties of an object.

FIG. 6 shows schematically and exemplarily a signal 25 (Doppler radar signal) in arbitrary units versus time received by the patch antenna 3.

During acquiring the signal 25 the patch antenna is attached to a bare chest of a patient.

Figure 3:
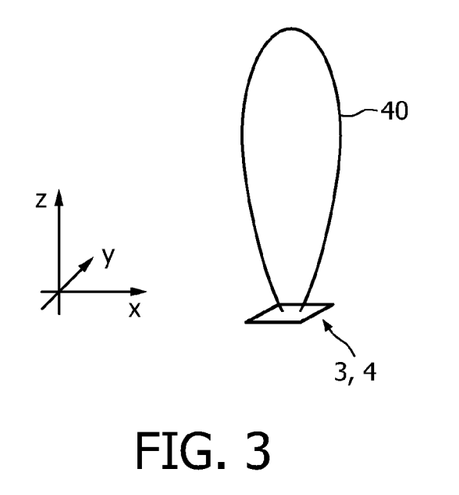
FIG. 3 shows schematically and exemplarily a main lobe of a single rectangular patch antenna.

FIG. 3 shows schematically and exemplarily a main lobe 40 of a radiation pattern of a single rectangular patch antenna 3 or 4. The main lobe 40 is substantially symmetric. In this embodiment, the patch antenna is located in the x-y plane and the main lobe protrudes perpendicularly from that plane.

Figure 4:
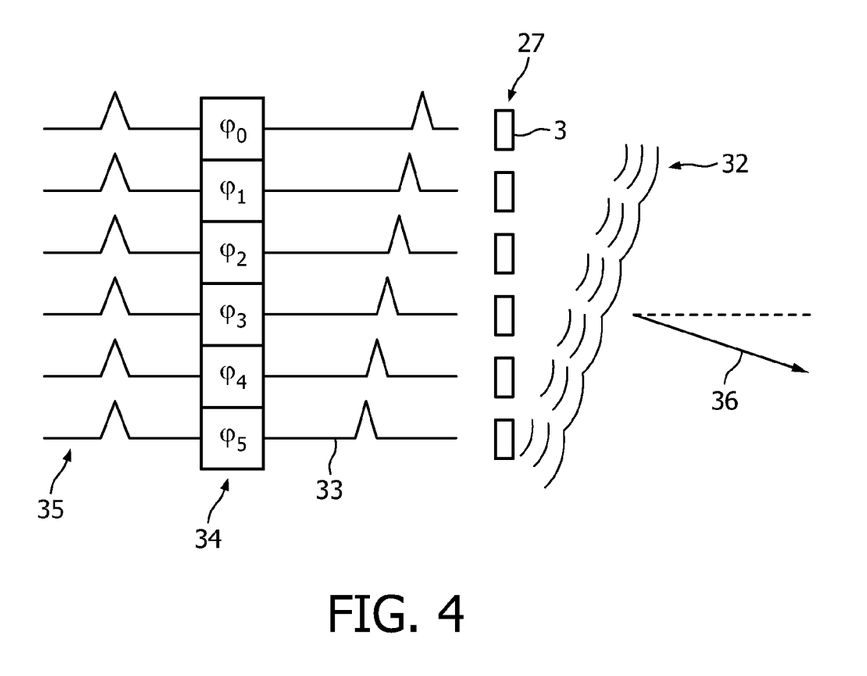
FIG. 4 shows schematically and exemplarily a working principle of phased array antennas.

FIG. 4 shows schematically and exemplarily an array configuration 27 comprising several patch antennas 3, in particular, comprising six patch antennas 3. The patch antennas 3 are adapted such that a substantially focused main lobe is generated, wherein there are several smaller side lobes present, but wherein most of the radiation is concentrated in the main lobe.

The array configuration of patch antennas 3 is preferentially adapted such that it is possible to sway the main lobe in different directions. This is preferentially achieved by introducing adjustable phase delays in the feeding lines of the several patch antennas 3 (phased array). The different phase delays can be used for beam-forming.

The main lobe can be directed in different directions using phase shifters 34 introducing a phase shift $\phi_0 \ldots \phi_5$ into excitation signals 35 of transmitters. The excitation signals 35 are inputted into the phase shifters 34. The phase shifters 34 shift the phases of the excitation signals 35 such that the radiation direction 36 of the radiation emitted by the patch antennas 3 points into a desired direction. The phase shifted signals are denoted with 33. By modifying the phase shifts $\phi_0 \ldots \phi_5$ the radiation 32, i.e. the wave front resulting from the patch antennas 3, can be emitted in a desired direction. For example, the phase shifts $\phi_0 \ldots \phi_5$ can be modified such that the radiation 32 is swayed. Using different phase shifts $\phi_0 \ldots \phi_5$, while receiving electromagnetic waves with such an antenna array configuration, results in the antenna configuration being sensitive in specific directions, while suppressing incoming signals from other directions. Thus, if electronically adjustable phase shifters 34 are used, it is possible to scan a given area for incoming electromagnetic waves without having to move the antenna array configuration mechanically.

Figure 5:
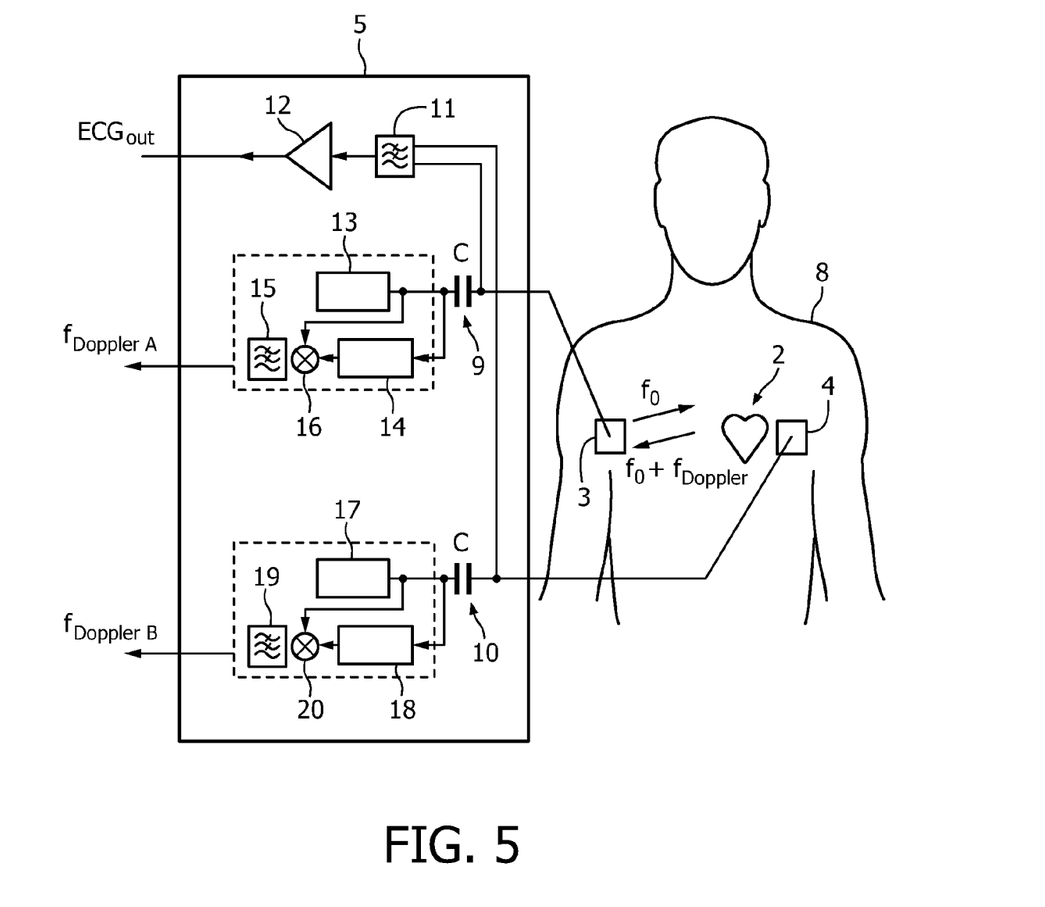
FIG. 5 shows schematically and exemplarily two patch antennas, an object and an electromagnetic wave generating and signal processing unit of the apparatus.

Referring again to FIG. 1, the patch antennas 3, 4 are connected to an electromagnetic wave generating and signal processing unit 5, wherein an embodiment of this electromagnetic wave generating and signal processing unit 5 is shown schematically and exemplarily and in more detail in FIG. 5.

The electromagnetic wave generating and signal processing unit 5 is adapted for generating electromagnetic waves, which are sent into the object via the patch antennas 3, 4, and for receiving electromagnetic waves reflected from the object via the patch antennas 3, 4. Furthermore, the electromagnetic wave generating and signal processing unit 5 is adapted for receiving signals from the electrically conductive element 21 of the patch antennas 3, 4, wherein the electrically conductive element 21 acts as an electrode. The electromagnetic wave generating and signal processing unit 5 processes the signals received from the patch antennas 3, 4 and, in particular, from the electrically conductive element 21 of the patch antennas 3, 4 such that an electrophysiological property and, in this embodiment, a mechanical property of the object can be determined.

In FIG. 5, the patch antennas 3, 4 are attached to a patient 8 for determining properties of a heart 2. The patch antennas 3, 4 are connected to the electromagnetic wave generating and signal processing unit 5.

The patch antenna 3 is connected to a capacitor 9 and a low-pass filter 11 of the electromagnetic wave generating and signal processing unit 5. The capacitor 9 is further connected to a transmitter 13 and a receiver 14 of the electromagnetic wave generating and signal processing unit 5. The electromagnetic wave generating and signal processing unit 5 further comprises a mixer 16 and a low-pass filter 15 for mixing signals from the transmitter 13 and the receiver 14 and for low-pass filtering the mixed signals. The mixed and low-pass filtered signal has a frequency $f_{Doppler,A}$ which can be described by following equation:

$$f_{Doppler,A} = \pm f_{0,A} \cdot \frac{2 \cdot v_A}{c}. \tag{5}$$

In equation (5), $f_{0,A}$ is the frequency of the electromagnetic waves sent by the transmitter 14 via the patch antenna 3 into the patient 8 and $v_A$ denotes the velocity of the movement of a part of the heart wall, from which the electromagnetic waves with the frequency $f_{0,A}$ are reflected.

The mixer multiplies the transmitted signal with the received signal. In particular, a multiplication of two signals with different frequencies can, for example, be described, by following equation:

$$\sin(f_x) \cdot \sin(f_y) = \frac{1}{2} \cdot (\cos(f_x - f_y) - \cos(f_x + f_y)) \tag{6}$$

wherein $f_x$ and $f_y$ are the different frequencies. Thus, the result of a mixing can be a signal with two components, one having the difference frequency $f_x - f_y$, and the other one having the sum frequency $f_x + f_y$. A low-pass filter takes away the component having the sum frequency. This means, if the object at which the electromagnetic waves are reflected does not move, there is no Doppler shift, i.e. no frequency difference between the two mixed signals, and therefore zero at the output of the low-pass filter. If the object moves indeed, then there is a Doppler shift, i.e. a frequency difference, and consequently a signal at the low-pass filter output.

The mixed and low-pass filtered signal with the Doppler frequency $f_{Doppler,A}$ is provided to a movement determination unit 7 of the apparatus 1 for determining movement values indicative for the movement of the object. In this embodiment, the movement determination unit 7 is adapted for viewing these movement values. For example, the movement determination unit 7 can calculate the velocity v of the movement of a part of the heart wall by using equation (5) and view this velocity, in particular together with the mixed and low-pass filtered signal received from the electromagnetic wave generating and signal processing unit 5. In this embodiment, the movement determination unit 7 receives two mixed and low-pass filtered signals from the two patch antennas 3 and 4, respectively, having the Doppler frequencies $f_{Doppler,A}$ and $f_{Doppler,B}$, respectively. In this embodiment, for each patch antenna 3, 4 a velocity of a part of the wall of the heart 2 is determined and viewed together with the respective mixed and low-pass filtered signals by the movement determination unit 7.

FIG. 6 shows schematically and exemplarily a Doppler radar signal 25, which can be the output of the low-pass filter 15 or the low-pass filter 19 described further below. The mechanical activity of the human heart is visible, because, if there is no mechanical activity of the heart, the signal 25 would substantially be a horizontal line. However, since the heart is beating, a peak in the signal 25 occurs at every heart beat.

The electromagnetic wave generating and signal processing unit 5 further comprises a second capacitor 10, which is connected to the patch antenna 4 and to a transmitter 17 and a receiver 18 of the electromagnetic wave generating and signal processing unit 5. Signals from the transmitter 17 and the receiver 18 are mixed by a mixer 20 and low-pass filtered by a low-pass filter 19. The mixed and low-pass filtered signal has the Doppler frequency $f_{Doppler,B}$ and is provided to the movement determination unit 7. The Doppler frequency $f_{Doppler,B}$ can be described by the following equation:

$$f_{Doppler,B} = \pm f_{0,B} \cdot \frac{2 \cdot v_B}{c}. \tag{7}$$

In equation (7), $f_{0,B}$ denotes the frequency of the transmitter 17 and $v_B$ denotes the velocity of the movement of a part of the wall of the heart 2, at which the electromagnetic waves transmitted by the transmitter 17 via the patch antenna 4 have been reflected.

An electromagnetic wave with the frequency $f_{0,A}$ is sent into the patient 8 using the transmitter 13, the capacitor 9 and the patch antenna 3. The electromagnetic wave is reflected by a part of the wall of the human heart 2 and the reflected electromagnetic wave, which has preferentially a frequency of $f_{0,A} \pm f_{Doppler,A}$, is received by the receiver 14 using the patch antenna 3 and the capacitor 9. Correspondingly, the transmitter 17 sends an electromagnetic wave with a frequency $f_{0,B}$ via the capacitor 10 and the patch antenna 4 into the patient 8, wherein the electromagnetic wave is reflected by a part of the wall of the human heart 2. It is preferentially assumed that the reflected electromagnetic wave has a frequency of $f_{0,B} \pm f_{Doppler,B}$. The reflected electromagnetic wave is received by the receiver 18 via the patch antenna 4 and the capacitor 10.

The electromagnetic wave generating and signal processing unit 5 further comprises a low-pass filter 11 for low-pass filtering electrocardiac signals, wherein the low-pass filter 11 is coupled between the capacitor 9 and the patch antenna 3 and between the capacitor 10 and the patch antenna 4. This way, the high frequency transmitted and received with the help of the antennas 3, 4 is prevented from invading the electrocardiogram amplifier 12. This amplifier 12 contained in the electromagnetic wave generating and signal processing unit 5 amplifies the low-pass filtered electrocardiac signal received from the low-pass filter 11. The low-pass filtered and amplified electrocardiac signal $ECG_{out}$ is provided to a viewing unit 6 for showing the electrocardiac signal.

The apparatus 1 is preferably used such that the electrically conductive elements 21 of the patch antennas 3 and 4 function as electrocardiac electrodes and that the patch antennas 3, 4 are both used for sending out and receiving electromagnetic waves, wherein the two patch antennas 3, 4 are preferably operating at different frequencies, so that they can operate simultaneously. However, running the patch antennas 3, 4 in a time-multiplex mode, such that only one is operating at a time is also possible. Furthermore, the apparatus 1 can be adapted such that only one of the patch antennas 3, 4 sends electromagnetic waves and the other of the patch antennas 3, 4 receives electromagnetic waves reflected from the object, in particular, from a part of the wall of the heart 2.

For the determination of a pre-ejection period as described later on, only one signal representative of the mechanical heart motion is required, i.e. it is sufficient to operate only one of the two electrodes as an antenna.

The low-pass filter 11 in front of the amplifier 12 keeps away the high-frequency components. Complementary, the capacitors 9, 10 represent a high-pass filter such that only the high frequencies of the electromagnetic waves can pass. In this way, the signals of the two measurement modalities can be separated.

By using the apparatus 1, an electrocardiogram and information on the mechanical action of the object 2, in particular, of a heart 2 of a patient 8, can simultaneously be determined. The patch antennas 3, 4 on the patient's chest operate simultaneously as electrocardiogram electrodes and as antenna for sending and receiving electromagnetic waves.

In FIGS. 1 and 8 two patch antennas 3, 4 having each an electrically conductive element 21 acting as electrode are used for measuring an electrocardiogram. However, for measuring an electrocardiogram or for performing another physiological measurement another number of antennas can be used. For example, a clinical 12-lead electrocardiogram requires ten electrodes on a patient body. In this case, ten antennas comprising an electrically conductive element as an electrode are preferentially used.

In the above described embodiment, rectangular patch antennas are used. But, in other embodiments, other kinds of patch antennas or other kinds of antennas can be used, which comprise an electrically conductive element acting as an electrode for electrophysiological measurements. For example, annular patch antennas can be used as, for example, described in "Microstrip and Printed Antenna Design", Randy Bancroft, ISBN: 1884932-58-4, Publisher: Noble-SciTech, 2004.

The apparatus 1 further comprises a property determination unit 36, which is connected to the viewing unit 6 and the movement determination unit 7. The property determination unit 36 is adapted for determining a property of the object, in particular, for determining the blood pressure and/or the arterial stiffness based on an electrocardiac signal measured by the electrically conductive element 21, which acts as an electrode, of the two patch antennas 3, 4 and based on a mechanical activity of the heart determined from the electromagnetic waves sent to and received from the object by the two patch antennas 3, 4.

Figure 7:
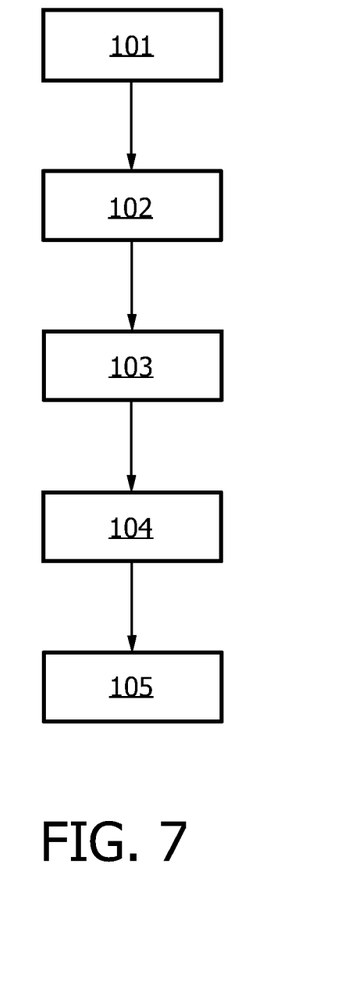

In the following an embodiment of a method for measuring properties of an object will be described with reference to a flow chart shown in FIG. 7.

In step 101, an electrocardiogram is measured by using the electrically conductive elements 21 of the patch antennas 3, 4 and simultaneously the transmitters 13, 17 send electromagnetic waves to the heart 2 of the patient 8 via the patch antennas 3, 4, wherein electromagnetic waves reflected from a part of the wall of the heart 2 are received by the receivers 14 and 18 via the patch antennas 3, 4.

In step 102, the electrocardiogram signal received by the electrically conductive elements 21 of the patch antennas 3, 4 is low-pass filtered by the low-pass filter 11 and amplified by the amplifier 12 and provided to the viewing unit 6. In addition, signals corresponding to the sent electromagnetic waves, which are sent by the respective transmitters 13, 17 via the patch antennas 3, 4, and signals corresponding to the electromagnetic waves, which have been reflected and which have been received by the receivers 14, 18 via the patch antennas 3, 4, respectively, are in each case mixed by the respective mixers 16, 20 and low-pass filtered by the respective low-pass filters 15, 19. The resulting signals with the Doppler frequency $f_{Doppler,A}$ and $f_{Doppler,B}$, respectively, are provided to the movement determination unit 7.

The movement determination unit 7 determines information about a movement of the object, in particular, about heart wall motion, from the signals received from the electromagnetic wave generating and signal processing unit 5, in step 103.

In particular, if the signals received from the electromagnetic wave generating and signal processing unit 5, wherein one of these signals can, for example, look like the signal shown in FIG. 6, are substantially flat lines, a movement of the human heart is substantially not present. The heart beats are represented by the peaks in the signals. The movement information is therefore preferentially the temporal position of the peaks of the signals, i.e. the temporal position of the heart beats. These peaks represent preferentially the mechanical activity of the heart.

In step 104, the property determination unit 36 for determining a property of the object determines a property, for example, the blood pressure, in particular based on the so-called pulse transit time. Since the electrical (electrocardiogram) and the mechanical action of the heart 2 is measured simultaneously, wherein a single sensor, i.e. a single patch antenna, is used for measuring the electrical and the mechanical action, the property determination unit 36 can determine the time the heart muscle needs to mechanically respond to the electrical excitation. This reaction time can be used for non-invasive cuff-less blood pressure measurements based on a measurement of the pulse transit time.

The pulse transit time is a period of time beginning when the pulse wave starts at the heart until it arrives at a certain part of the body, for example, a finger. The pulse transit time depends on several physiological parameters, wherein one of these physiological parameters is the blood pressure. Therefore, by measuring the pulse transit time it is possible to calculate the current blood pressure, if the other physiological parameters are known. Thus, the property determination unit 36 can be adapted for determining the current blood pressure non-invasive and cuff-less.

In particular, the moments in time when peaks occur in the radar signal representing the mechanical activity of the heart are compared to the moments in time when the peaks in the electrocardiogram signal occur. The electrocardiogram is the electrical excitation of the heart, so it all starts with the peak in the electrocardiogram. Then it takes a while until the heart muscle reacts to this excitation and starts to contract. So the heart starts to build up pressure, but at first, nothing happens, because the pressure in the arterial system is higher. Only after a while during which the heart muscle contracts more and more, the pressure inside the heart is so high, that it finally exceeds the arterial pressure, and then the heart valves open and mechanical motion occurs. So there is a significant delay between the peak in the electrocardiogram and the peak in the radar signal representing the mechanical action, and this timely difference is called "Pre-ejection period". Both signals are measured simultaneously. The peaks in both, electrocardiogram and radar signal, are detected and the timely difference (the pre-ejection period) is calculated.

The blood pressure can be determined from the pulse transit time by determining the peaks in the electrocardiogram as the starting points of the pulse wave at the heart, and by measuring, in particular optically, the arrival time of the pulse wave, for example, at the finger tip. The higher the blood pressure, the shorter the travel time from heart to finger.

Generally, the peak in the electrocardiogram doesn't indicate the true starting time of the pulse wave at the heart, because of the pre-ejection period explained above. This can be expressed by following equation:

$$PAT = PEP + PTT \quad (8)$$

wherein the pulse arrival time PAT is the pre-ejection period PEP plus the pulse transit time PTT (for example travel time from heart to finger).

The pre-ejection period can be determined by looking simultaneously at the electrical excitation of the heart and its mechanical response as performed in step 101.

Thus, preferentially in step 104 the pre-ejection period PEP is determined and used in order to allow a precise blood pressure indication with the help of measuring the PAT, which is preferentially also measured in step 101, but which can, in another embodiment, also be measured before or after performing step 101.

If PAT and PEP are known, PTT can be calculated according to equation (8), and from the PTT, the blood pressure BP can be derived for example using the calibration equation:

$$BP = A \cdot \frac{1}{PTT} + B. \quad (9)$$

Blood pressure BP is inversely proportional to the PTT, and A and B are calibration factors. This blood pressure determination is described in more detail in Muehlsteff, J.; Aubert, X. L.; Schuett, M.: "Cuffless Estimation of Systolic Blood Pressure for Short Effort Bicycle Tests: The Prominent Role of the Pre-Ejection Period"; Engineering in Medicine and Biology Society, 2006. EMBS apos; 06. 28th Annual International Conference of the IEEE, August 2006 Page(s): 5088-5092, which is herewith incorporated by reference.

Thus, preferentially in step 101 the electrocardiogram and the mechanical heart activity are measured simultaneously.

Then, after step 102, the peaks in the radar signals are determined as information about a movement of the heart in step 103.

In step 104, the peaks in the electrocardiogram are determined and the timely difference between the peaks in the electrocardiogram and in the radar signals is calculated, which is the pre-ejection period PEP. The true travel time of the pulse wave from heart to finger, i.e. the pulse transit time, is calculated using equation (8) and translated into the blood pressure using equation (9), wherein for calculating the pulse transit time an additional measurement, in particular an additional optical measurement, is performed, for example, at the finger tip, that detects the arrival of the pulse waves in the finger. This measurement is preferentially performed in step 101.

As already mentioned above, it is generally assumed that a peak in an electrocardiogram is the moment in time, when the pulse wave starts at the heart. However, due to the reaction time of the heart muscle that it takes to respond to the electrical excitation, this is not true. The time between the peak in the electrocardiogram and the actual start of the pulse wave is called the pre-ejection period. Thus, preferentially, the pulse transit time measured by using an electrocardiogram has to be corrected by subtracting the pre-ejection period, in order to obtain a more precise blood pressure value from the further calculations using the pulse transit time. In one embodiment, the pre-ejection period is estimated and the estimated pre-ejection period is subtracted. But, it is more preferred, as already mentioned above, that the pre-ejection period is determined by the property determination unit 36, in particular, for every single heart beat, in order to improve the accuracy of the pulse transit time and, thus, of the determined current blood pressure.

Although in the above described embodiment, the electrically conductive element 21 of antenna 3, 4 is used for measuring an electrocardiogram, in other embodiments, any other electrophysiological measurement can be performed, which uses electrodes, wherein the electrodes are the electrically conductive elements of the antennas, for example, impedance-cardiography or bio-impedance measurements, in particular, in order to get additional physiological information without having to use additional sensors.

By using an embodiment of the invention, two complementary measurement modalities can be combined in a single sensor, wherein two measurement modalities can be used simultaneously. Furthermore, any electrophysiological measurement employing electrodes on the skin can be enhanced, especially without additional on-body sensors. In addition, if used in an electrocardiogram measurement setup, the antennas with the electrically conductive elements allow for capturing a complete picture of the heart performance, i.e. electrically excitation and mechanical activity of the heart, as well as enabling non-invasive cuff-less blood pressure measurements and determining arterial stiffness. Furthermore, handling and ease-of-use for a patient in a personal health care setting can be improved and the measurement system can be simplified, reducing the risk of misuse by a patient in a personal health care setting. Moreover, system costs can be reduced by saving sensors and accessories.

Arterial stiffness is one of the parameters that influence the PTT, next to blood pressure. In the above mentioned equation (9) arterial stiffness is contained in the calibration factors A and B. While blood pressure can change quickly, arterial stiffness is rather constant. It is sometimes used as an indicator for the "age" of the arteries, because the arteries become stiffer while we grow older. Thus, in an embodiment, the current blood pressure is determined with the help of another method, e.g. a blood pressure cuff, and then an indicator for arterial stiffness is calculated from the equation (9) using the measured PTT. This is described in more detail, for example, in "Arterial Stiffness Estimation in Hypertension", Juan Du, Gangmin Ning, Yingqi Li, Xiaoxiang Zheng, Engineering in Medicine and Biology Society, 2005, IEEE-EMBS 2005. 27th Annual International Conference of the Volume, Issue, 2005, Page(s): 5507-5510, which is herewith incorporated by reference.

Preferentially, the frequency of the electromagnetic waves is much higher than the general electrocardiogram bandwidth (0.67 Hz ... 150 Hz), i.e. the frequency of the electromagnetic waves is preferentially one or several orders of magnitude higher than the frequency of the electrophysiological measurement, which uses the electrically conductive element as an electrode. This allows separating the two measurements easily with the help of filters.

The electromagnetic waves reflected at the object, in particular, at the wall of the heart, carry information on the mechanical activity of the object, in particular, carry information on the mechanical activity of the heart. In the following equation, $\Theta_k(t)$ is the timely varying phase caused by a reflecting surface with a relevant velocity component $v_k(t)$, and $\Xi_k$ is the sensor-reflector distance:

$$\Theta_k(t) = \frac{4\pi}{\lambda}\left(\int_0^t v_k(t')dt' + \Xi_k\right) \quad (10)$$

Equation (10) can be used for determining information on the mechanical activity. Such a determination of mechanical activity is described in more detail in J. A. J. Thijs, J. Muehlsteff, R. Pinter, "The use of a two channel Doppler Radar Sensor for the characterization of heart motion phases", IEEE EMBC 2006, which is therewith incorporated by reference.

Although in the above mentioned embodiments the object is preferentially a human heart within a human patient, in another embodiment, the apparatus, the method and the computer program for measuring properties of an object can be adapted for measuring properties of an animal, in particular, of a part of an animal. For example, the antenna can be used for measuring the mechanical activity of the heart of an animal and the electrically conductive element of the antenna can function as an electrode for measuring an electrocardiogram of the heart of the animal, wherein preferentially two antennas comprising each an electrically conductive element for functioning as an electrode are used.

Other variations to the disclosed embodiments can be understood and effected by those skilled in the art and practicing the claimed invention, from a study of the drawings, the disclosure, and the appended claims.

In the claims the word "comprising" does not exclude other elements or steps and the indefinite article "a" or "an" does not exclude a plurality.

A single processor or other unit may fulfill the functions of several items recited in the claims. The mere fact that certain measures are recited in mutually different dependent claims does not indicate that a combination of these measures cannot be used to advantage.

Determinations and calculations, like the determination of information about a movement of the object or the determination of a property of the object using the result of an electrophysiological measurement and the result of a measurement using the electromagnetic waves, performed by one or several units or devices can be performed by any other number of units or devices. For example the functions of the movement determination unit 7 and the property determination unit 36 and preferentially of the viewing unit 6 can be performed by a single unit or by any other number of units. The calculations and determinations and/or a control of the apparatus in accordance with a method in accordance with the invention can be implemented as program code means of a computer program and/or as dedicated hardware.

A computer program may be stored/distributed on a suitable medium, such as an optical storage medium or a solid-state medium supplied together with or as part of other hardware, but may also be distributed in other forms, such as via the internet or other wired or wireless telecommunication systems.

Any reference signs in the claims should not be construed as limiting the scope of the invention.

The invention claimed is:

1. An apparatus for measuring properties of a moving object in a patient, wherein the apparatus comprises:
   one or more antennas configured to send electromagnetic waves to the moving object and which receive Doppler shifted electromagnetic waves reflected from the moving object; and
   a movement determination unit configured to determine movement information correlated to a movement of the object based on the Doppler shifted electromagnetic waves, wherein the one or more antennas comprise an electrically conductive element configured to detect an electrical signal having a frequency which differs from a frequency of the electromagnetic waves sent by the antenna and the Doppler shifted electromagnetic waves received from the moving object, wherein the one or more antennas are configured to function as an electrode to measure a second property of the object.

2. The apparatus as defined in claim 1, wherein the electrically conductive element is a metal plate.

3. The apparatus as defined in claim 1, wherein the electrically conductive element is adapted for an electrocardiogram measurement.

4. The apparatus as defined in claim 1, wherein the apparatus comprises a plurality of the antennas, wherein at least one of the plurality of the antennas is configured for at least one of sending and receiving electromagnetic waves at a frequency, which differs from a frequency of electromagnetic waves of another of the plurality of antennas.

5. The apparatus as defined in claim 1, wherein the apparatus comprises a plurality of antennas which are adapted for forming a beam of the electromagnetic waves by using a phased array of the antennas.

6. The apparatus as defined in claim 1 wherein the antenna is configured to be attached to a surface of the patient for preventing a relative movement between the surface and the antenna.

7. The apparatus as defined in claim 1, wherein the second property of the object which is measurable by detecting the electrical signal by the electrically conductive element is an electrocardiac signal.

8. The apparatus as defined in claim 1 wherein the object is a heart of the patient, wherein the apparatus comprises a property determination unit for determining at least one of a blood pressure and an arterial stiffness based on an electrocardiac signal measured by the electrically conductive element functioning as an electrode of at least two of the antennas and based on a mechanical activity of the heart determined from the electromagnetic waves sent to and received from the object by the at least two of the antennas.

9. The apparatus as defined in claim 1 further comprising an electromagnetic wave generating and signal processing unit electrically connected to at least one of the one or more antennas and comprising a capacitor, a low-pass filter, and an amplifier, the low-pass filter connected between and electrically connected to the antenna and amplifier.

10. The apparatus as defined in claim 9, wherein the second property of the object is an electrocardiac signal having a frequency lower than a higher frequency of the Doppler shifted, reflected electromagnetic waves, and wherein the low-pass filter prevents the higher frequency Doppler shifted, reflected electromagnetic waves from invading the amplifier.

11. The apparatus as defined in claim 10, wherein the wave generating and signal processing unit further comprises a high-pass filter and a receiver.

12. The apparatus as defined in claim 11, wherein the high-pass filter is connected between and electrically connected to the antenna and receiver such that only the higher frequency Doppler shifted, reflected electromagnetic waves can pass to the receiver.

13. The apparatus as defined in claim 12, wherein the wave generating and signal processing unit further comprises a transmitter, mixer, and second low-pass filter, wherein the mixer mixes a signal from the transmitter with a signal from the receiver to produce a mixed signal and the second low-pass filter filters the mixed signal to produce an output signal.

14. The apparatus as defined in claim 1, wherein the apparatus comprises a plurality of the antennas, wherein the plurality of the antennas is run in a time-multiplex mode, such that when a one antenna of the plurality of antennas is operating, the one antenna is the only antenna operating.

15. A method for measuring properties of a moving object in a patient comprising:
    sending electromagnetic waves to the moving object with an antenna comprising an electrically conductive element configured for connection to the patient, the moving object reflecting the electromagnetic waves causing a Doppler shift in the reflected electromagnetic waves;
    receiving the Doppler shifted, reflected electromagnetic waves with the conductive element of the antenna;
    analyzing the Doppler shifted, reflected electromagnetic waves to determine movement information indicative of a movement of the moving object;
    with the electrically conductive element of the antenna, receiving from the object an electric signal having a frequency different from a frequency of the Doppler shifted, reflected electromagnetic waves; and
    determining a second property the object from the received electric signal.

16. A non-transitory computer readable medium containing a computer program for measuring properties of an object, wherein the computer program comprises program code configured for causing a computer to carry out the steps of the method as defined in claim 15, when the computer program is run on a computer.

17. An apparatus for measuring mechanical movement and an electrocardiogram of a heart in a patient comprising:
    a first antenna configured to be connected with the patient, to send electromagnetic waves toward the heart, to receive Doppler shifted electromagnetic waves reflected by a first surface of the heart, and to receive electrocardiogram signal;
    a second antenna configured to be connected with the patient, to send electromagnetic waves toward the heart, to receive Doppler shifted electromagnetic waves reflected by a second surface of the heart, and to receive electrocardiogram signals;
    a wave generating and processing unit comprising:
        a first transmitter electrically connected with the first antenna and configured to cause the first antenna to transmit the electromagnetic waves;
        a second transmitter electrically connected with the second antenna and configured to cause the second antenna to transmit the electromagnetic waves;
        a first signal processing unit electrically connected to the first antenna configured to receive the Doppler shifted electromagnetic waves and the first transmitter to receive the transmitted electromagnetic waves and configured to output a first Doppler shift signal;
        a second signal processing unit electrically connected to the second antenna configured to receive the Doppler shifted electromagnetic waves and the second transmitter to receive the transmitted electromagnetic waves and configured to output a second Doppler shift signal; and
        an electrocardiogram output circuit electrically connected to the first and second antennas and including a filter which separates the electrocardiogram signal from the Doppler shifted electromagnetic waves and is configured to output the electrocardiogram signal; and
    a movement determining unit which processes the electrocardiogram signal from the electrocardiogram output circuit and the first and second Doppler shift signals from the first and second signal processing units and which is configured to generate information about heart wall motion.

18. The apparatus as defined in claim 17, wherein the first and second signal processing units include an amplifier, a first filter for blocking the electrocardiogram signal, a receiver, a mixer, and a second filter configured for separating the Doppler shift signal from the electromagnetic waves.

\* \* \* \* \*